United States Patent
Stokowski et al.

(10) Patent No.: US 6,727,512 B2
(45) Date of Patent: Apr. 27, 2004

(54) METHOD AND SYSTEM FOR DETECTING PHASE DEFECTS IN LITHOGRAPHIC MASKS AND SEMICONDUCTOR WAFERS

(75) Inventors: Stan Stokowski, Danville, CA (US); Damon F. Kvamme, San Jose, CA (US); Chun Shen Lee, Cupertino, CA (US); Donald W. Pettibone, San Jose, CA (US)

(73) Assignee: KLA-Tencor Technologies Corporation, Milpitas, CA (US)

( * ) Notice: Subject to any disclaimer, the term of this patent is extended or adjusted under 35 U.S.C. 154(b) by 0 days.

(21) Appl. No.: 10/289,005

(22) Filed: Nov. 5, 2002

(65) Prior Publication Data

US 2004/0016897 A1 Jan. 29, 2004

Related U.S. Application Data

(63) Continuation-in-part of application No. 10/094,305, filed on Mar. 7, 2002, now Pat. No. 6,646,281.
(60) Provisional application No. 60/412,626, filed on Sep. 20, 2002.

(51) Int. Cl.[7] ................................................. G01B 9/02
(52) U.S. Cl. ................................. 250/559.45; 348/125
(58) Field of Search ........................ 250/548, 559.45, 250/559.46; 348/125, 126, 128; 356/399–401, 237.1–237.5, 394; 382/144

(56) References Cited

U.S. PATENT DOCUMENTS

| | | | | |
|---|---|---|---|---|
| 5,430,548 A | * | 7/1995 | Hiroi et al. | 356/394 |
| 6,134,014 A | * | 10/2000 | Tzu et al. | 356/450 |
| 6,248,988 B1 | * | 6/2001 | Krantz | 250/201.3 |
| 6,327,033 B1 | * | 12/2001 | Ferguson et al. | 356/394 |
| 6,584,218 B2 | * | 6/2003 | Wihl et al. | 382/144 |
| 2001/0019625 A1 | | 9/2001 | Kenan et al. | 382/144 |

* cited by examiner

Primary Examiner—Stephone B. Allen
(74) Attorney, Agent, or Firm—Beyer Weaver & Thomas, LLP

(57) ABSTRACT

Provided are apparatus and methods for detecting phase defects. The invention relies generally on the distortion of light as it passes through defects in phase shift masks to detect these defects. Light traveling through a defect, such as a bump in an etched area will travel at a different angle than light traveling through air. In order to enhance the signals generated from the defects, the invention in several embodiments provides a multiple element detector having at least four elements, arranged in a radially symmetric configuration. Individual elements of the detector are selected to form a differential signal based on the configuration of pattern lines in the area proximate to the defect. The resulting differential signal is used to generate an image signal and to identify phase defects.

43 Claims, 9 Drawing Sheets

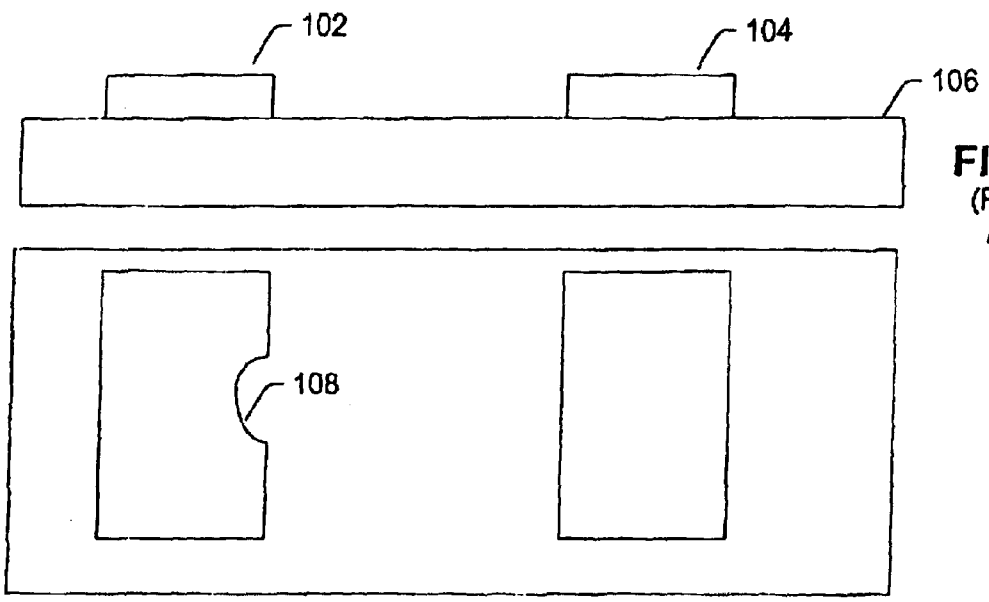
FIG. 1A
(PRIOR ART)
FIG. 1B
(PRIOR ART)
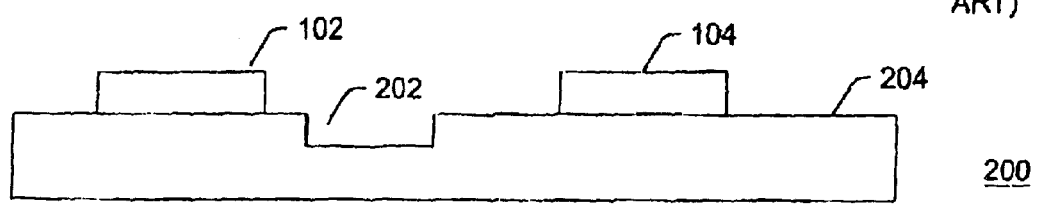
FIG. 2A
(PRIOR ART)
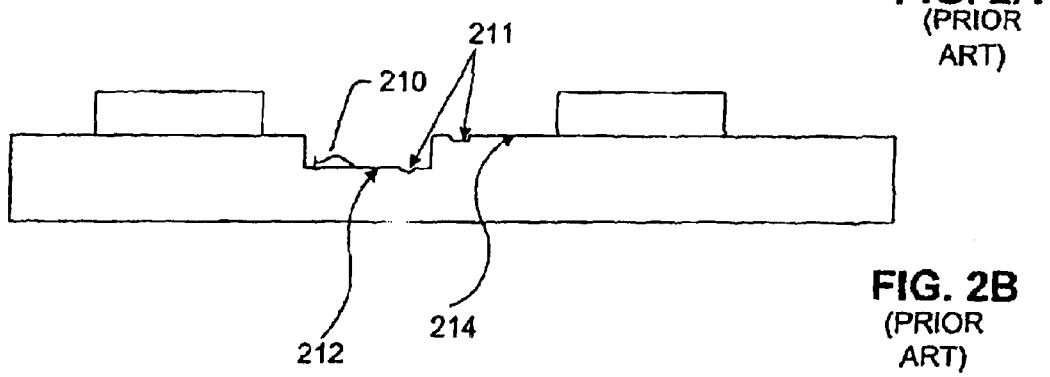
FIG. 2B
(PRIOR ART)

Schematic Layout of Zernike Phase Contrast Microscope

METHOD AND SYSTEM FOR DETECTING PHASE DEFECTS IN LITHOGRAPHIC MASKS AND SEMICONDUCTOR WAFERS

CROSS-REFERENCE TO RELATED APPLICATION

This application claims priority of U.S. Provisional Patent Application No. 60/412,626 filed Sep. 20, 2002, which application is incorporated herein by reference in its entirety for all purposes.

This application is a continuation-in-part of U.S. Nonprovisional application Ser. No. 10/094,305 filed Mar. 7, 2002 now U.S. Pat. No. 6,646,281 entitled, "DIFFERENTIAL DETECTOR COUPLED WITH DEFOCUS FOR IMPROVED PHASE DEFECT SENSITIVITY" by Matthias C. Krantz, Donald W. Pettibone, Damon F. Kvamme and Stan Stokowski. Applicant claims benefit of the earlier filing date of the nonprovisional application, pursuant to the provisions of 35 U.S.C. 120.

BACKGROUND OF THE INVENTION

The present invention relates to methods and apparatus for detecting defects in masks used in semiconductor processing. More particularly, the present invention relates to apparatus and methods for detecting defects in phase shift masks.

Fabrication of semiconductor wafers typically relies on photolithography to produce circuit patterns on layers of a wafer. The wafer is coated with a "photoresist". Light is then transmitted through the mask and imaged onto the wafer. Photoresist is a material which is sensitive to light. A negative photoresist cures or hardens when exposed to light, so that the unexposed areas can be washed away. For example, in one system, ultraviolet light is used to expose a portion of the photoresist layer. A positive photoresist reacts in the opposite manner, the exposed regions can be washed away. The photoresist that is left acts as a mask, so that materials may be deposited in the areas not covered by photoresist to thereby form patterns on the wafer. The photoresist is then removed.

Designers and manufacturers constantly strive to develop smaller devices from the wafers, recognizing that circuits with smaller features generally have greater speeds and increased yield (numbers of usable chips produced from a standard semiconductor wafer). Photolithography equipment manufacturers have generally employed equipment using progressively smaller wavelengths to a current size below 193 nm in order to achieve smaller feature sizes. However, as the size of the circuit features decrease, physical limits such as the convergence between the wavelength of the light used to create the photoresist mask and the wafer feature sizes present obstacles to further reduction in feature size using the same semiconductor fabrication equipment.

Designers of such equipment have discovered that a phase shift mask (PSM) will allow the patterning of smaller features, even as the feature size approaches the wavelengths of the light used to create the photoresist pattern from the PSM. In some cases the use of a PSM may decrease the minimum feature size by a factor of two. With PSM, the mask no longer looks like the design shapes. Instead, the PSM contains shapes which cause the design shapes to appear as a result of constructive and destructive interference of light passing through the PSM. Alternating phase shift masks generally use an etching technique to etch a small depression into the mask. Light passing through the depression experiences a phase shift relative to the unetched areas, creating sharper images at the wafer. While the overall process uses particular design rules for minimum feature size, a PSM allows circuits with more aggressive critical dimensions to be consistently built using existing lithography tools.

Due to their importance in decreasing feature size while using existing equipment, semiconductor and semiconductor equipment manufacturers are highly motivated to detect PSM defects. Given the small size of the features and the volumes of wafers to be produced from a mask, it is essential that defects be detected in the masks to either enable repairs, where appropriate, of the mask or discard unsalvageable masks prior to production.

Conventional inspection techniques such as optical methods work well in identifying defects of typical chrome on glass masks. These defects include the placement of chrome in unintended places and the absence of chrome portions where desired. A conventional chrome on glass mask is shown in FIGS. 1A and 1B. FIG. 1A shows a cross section with chrome sections 102 and 104 deposited on transparent layer 106. A typical material for layer 106 is quartz, due to its ability to transmit light. FIG. 1B is a top view of the photomask showing a typical defect 108. Conventional optical inspection techniques work well in identifying such defects because the amplitude of the light transmitted through the defect is directly affected, i.e., the absence of the normally opaque chrome section allows light to be transmitted and detected in a location where such detection is unexpected. Contaminants on the glass can be identified by using either transmitted or reflected light or a combination of the two. The defects directly affect the amplitude of light passing through and reflected from the mask and are amenable to measurement by the above referenced conventional techniques.

Phase shift defects, however, present unusual problems. Imaging of phase objects and detection of phase defects typically requires special imaging methods to convert the phase information into intensity differences at the imaging detector. Numerous methods have been proposed to accomplish this including the Zernike phase contrast, differential interference contrast (DIC), differential phase contrast (DPC), defocused imaging, and interferometric techniques. Most of these methods involve changing the phase delay of the optical wavefront in the pupil plane of the imaging system in a way that will produce the greatest intensity effect at the detector for a given phase defect or phase object. The optimum method greatly depends on the phase shifts present in the object. In biological samples weak phase shifts need to be imaged. In phase shift masks for photolithography strong phase shifters are used. As a result, a sensitive defect detection system for phase defects on phase shift masks must detect weak phase objects in the presence of strong phase and amplitude objects. Of particular interest in the design is the response of a system to phase edges, such as in detecting phase defects next to chrome quartz edges. Another important aspect for automated photomask inspection systems is whether the system response to phase objects is isotropic in the plane of the object. An anisotropic response as yielded by the DIC or a Nomarski technique or the linear DPC technique may be acceptable for visual inspection but complicates automated inspection.

For the foregoing reasons, there is a need for improved methods and apparatus capable of detecting phase shift mask defects in the presence of both strong amplitudes and phase shifts. In particular, an improved method is needed for detecting phase defects near chrome edges or etched quartz edges.

SUMMARY OF THE INVENTION

To achieve the foregoing, the present invention provides apparatus and methods for detecting phase defects.

The invention relies generally on scanner type imaging systems and detects phase defects on photomasks by their modification of the light passing through the mask. Much of the detail provided in the specification for practicing the invention is given for scanners. Those skilled in the art, having the benefit of the details provided in this specification, will appreciate that the invention may also be implemented on projector type imaging systems.

Specifically, in one group of embodiments, the invention relies on the modification of the phase of the wavefront at the pupil plane of the optical imaging system using a multiple element detector having at least four elements in conjunction with the differential detection of the image intensity from selected elements of the detector. In general, the multiple elements are in a configuration having at least one element in each of the quadrants of a detector, the combination of elements configured to selectively provide a differential signal in at least the horizontal, vertical, and diagonal directions. In order to enhance the signals generated from phase defects located near pattern edges, such as on a photomask, a differential signal from the selected detector elements is obtained.

In one embodiment, a method for detecting phase defects in a semiconductor processing photomask is disclosed. A light beam reflected from or transmitted through the semiconductor processing photomask or wafer is collected at a detector comprising at least 4 elements. At least one element is used to generate a first signal and at least one of the other elements is used to generate a second signal. The elements for the first and second signals are selected to correspond to the orientation of opaque pattern lines on the photomask and thus to increase the sensitivity of the defect signal. The first and second signals are combined to form a differential signal, indicative of the presence or absence of a defect.

In another embodiment, selection of the detector elements to form the first and second signals is performed using programmed logic contained within a general purpose computer, microprocessor, or FPGA coupled to the detector elements. In a specific embodiment, selection of detector elements and generation of an image element from the first and second elements is repeated at a plurality of locations on the photomask to generate an image signal. The image signal is compared to an image signal from a similar pattern location on one of a same die on the photomask, another die on the photomask, or a pattern from a design database to identify defects.

These and other features and advantages of the present invention are described below with reference to the drawings.

BRIEF DESCRIPTION OF THE DRAWINGS

The present invention will be readily understood by the following detailed description in conjunction with the accompanying drawings, wherein like reference numerals designate like structural elements, and in which:

FIGS. 1A and 1B illustrate a conventional chrome on glass photomask.

FIGS. 2A and 2B depict a cross section of a photomask with etched phase shift sections.

DETAILED DESCRIPTION OF SPECIFIC EMBODIMENTS

Figure 3:
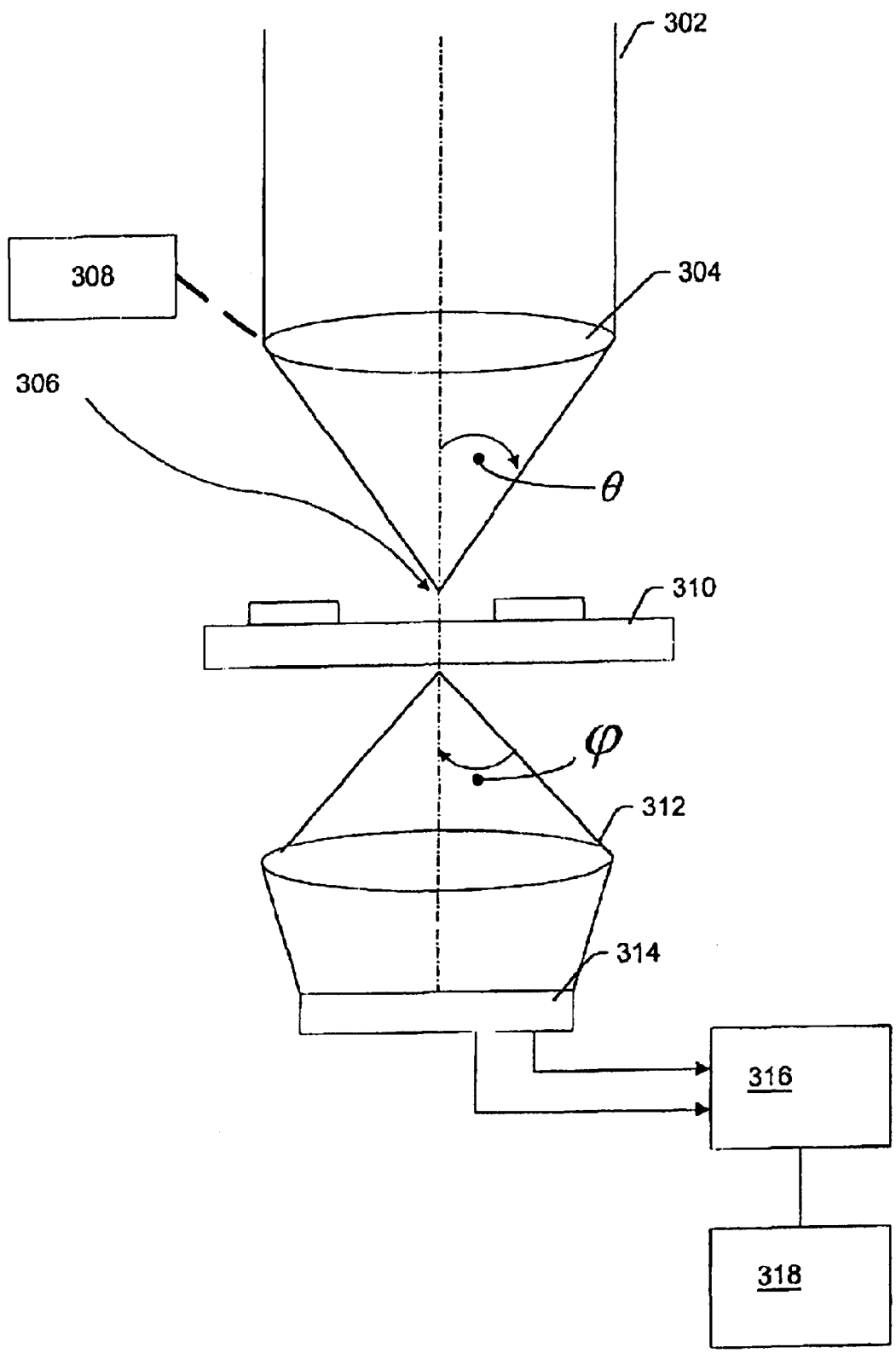
FIG. 3 is a diagram of a scanning optical microscopy system in accordance with one embodiment of the present invention.

Reference will now be made in detail to specific embodiments of the invention. Examples of these embodiments are illustrated in the accompanying drawings. While the invention will be described in conjunction with these specific embodiments, it will be understood that it is not intended to limit the invention to these embodiments. On the contrary, it is intended to cover alternatives, modifications, and equivalents as may be included within the spirit and scope of the invention as defined by the appended claims. In the following description, numerous specific details are set forth in order to provide a thorough understanding of the present invention. The present invention may be practiced without some or all of these specific details. In other instances, well known process operations have not been described in detail in order not to unnecessarily obscure the present invention.

Several embodiments of the present invention rely on the phase shifting caused by defects to detect their presence in a phase shift mask. Phase shift masks change the phase of the light waves travelling through the mask to expose the photoresist layer on the semiconductor wafer. The phase shifting (e.g., by 180 degrees) causes cancellation in particular portions of the light passing through the mask, thus allowing the printing of smaller features. FIG. 2A is a cross section of an alternating phase shift mask 200. The phase shift results from the etched portion 202 of the quartz mask material 204. Light transmitted through the etched portion experiences an advanced phase shift relative to light transmitted through the unetched portions of mask material 204. A typical etch depth for etch portion 202 is about one wavelength to produce a 180 degree phase shift in a mask with refractive index of 1.5, i.e. about 250 nm. Example defects can include a bump (e.g., 210 shown in FIG. 2B), when the etch does not proceed to the full depth in one or more areas, and a divot (e.g., 211), which may be located on both the etched surface 212 and unetched surface 214. The detection techniques of the present invention take advantage of the diffraction of the incident field when travelling through defects such as bumps 210 or divots 211.

The invention generally provides increased phase defect sensitivity by splitting a detector into segments, each segment capable of providing separate signals. In a first group of embodiments, the detector is split into annular regions and improved phase contrast results from detection using a differential signal from the detector segments coupled with defocusing. In a second group of embodiments, improved phase contrast results from the detector split into segments with at least one segment representative of each of four quadrants of the detector coupled with selective selection of the segments to correspond to configurations of the pattern lines surrounding the area to be inspected for defects. The invention relies generally on scanner type imaging systems and detects phase defects on photomasks by their modification of the light passing through the mask. Much of the detail provided in the specification for practicing the invention is given for scanners. Those skilled in the art, having the benefit of the details provided in this specification, will appreciate that the principals of the invention may also be implemented on projector type imaging systems.

Specifically, in a first group of embodiments, the invention relies on the modification of the phase of the wavefront at the pupil plane of the optical imaging system using defocus in conjunction with the differential detection of the image intensity from different annular segments of a detector in the detector plane.

Further, in a second group of embodiments, the invention relies on the modification of the phase of the wavefront at the pupil plane of the optical imaging system using a multiple element detector having at least four elements in conjunction with the differential detection of the image intensity from selected elements of the detector. In general, the multiple elements are in a configuration having at least one element in each of the quadrants of a detector, the combination of elements configured to selectively provide a differential signal in at least the horizontal, vertical, and diagonal directions. In order to enhance the signals generated from phase defects located near pattern edges, such as on a photomask, a differential signal from the selected detector elements is obtained.

In a conventional imaging microscope the equivalent step to having a segmented detector would be to have a segmented illumination source, which would then require either multiple passes with different illumination sectors or use of some other technique, relying on polarization for instance, to be able to separate the images obtained from different illumination sectors. The scope of the present invention is intended to cover projector type imaging systems as well as scanning image systems using the principals described herein. That is, the present invention is intended to be extended to projection imaging inspection systems wherein the single illumination source and multi segmented detector is replaced with a multi-segmented illumination source and capturing the signal at a common detector location, for example in one instance, at different times to correspond to different illumination positions sequentially activated.

A diagram of an optical scanning microscope system employing detection methods of the present invention is shown in FIG. 3. However, the techniques of the present invention may be implemented with any suitably configured detection system, and the system of FIG. 3 is not meant to narrow the scope of the invention. These techniques may be applied to all types of phase shift masks. For example, the techniques described may be applied to alternating phase shift masks, attenuated (tritone) masks, and to binary masks. The incident light inspection beam 302 converges after transmission through objective lens 304 to a focal point 306. The location of the focal point may be selected through the use of controller 308. One skilled in the art would recognize that various means may be used to control the location of the focal point without departing from the concepts of the invention disclosed herein. For example, a stepper motor could be used to move objective lens 304 in order to locate the focal point 306 at a desired location with respect to mask 310. Moreover, it should be understood that the principles of the present invention may be extended to include manual mechanisms (as well as automatic mechanisms) of selecting the focal point 306. For example, such manual mechanisms of controlling the location of the focal point 306 may include rigidly fastening the objective lens at a desired distance from mask 310 prior to any inspections. As will be discussed further with respect to the different embodiments below, the first group of embodiments, for example those illustrated in FIGS. 4A–C generally rely on a differential signal detected on a detector split into annular areas coupled with defocusing. By using this configuration, the images produced using the detector signals are isotropic. That is, the detected signal sensitivity is equal in all directions and the increased sensitivity is obtained using defocusing. In accordance with a second group of embodiments, the inspection beam 302 need not be defocused and preferably is focused on the surface of the mask 310.

The inspection light beam 302 is shown transmitted through mask 310 to collector 312. Collector 312 collects the light onto a detector 314 over a range of angles. In conventional systems photo detector 314 sums all intensities of light waves received over the full area of the detector. The objective lens angle θ and the collection angle φ determine in part the signals generated at the detector. Generally the relationship between the collection angle φ and the objective lens angle θ is represented by σ (sigma), which, for an air medium, is defined as follows:

$$\sigma = \sin \phi / \sin \theta$$

Conventional optical inspection systems employ relatively wide objective lens angles and collection angles, both typically approximating 45° and resulting in a sigma value approximating 1. However, large sigma values have been shown to wash out signals relating to phase defects. The present invention, in several embodiments, increases the sensitivity to signals related to phase defects by collecting the light waves onto a detector 314 split into regions or zones (e.g., radially symmetric or concentric regions). In practice, it has been observed that higher intensity signals regarding phase defects are produced when the sigma is lower. Sigma values in the range of 0.2 to 0.7 produce suitable results.

Different zones in the detector 314 correspond to different angles or spatial frequency components of the diffracted light being collected. What is meant here by the use of the term signal is the change in detected signal between an object that has a phase defect and an otherwise identical object without the phase defect, i.e. a difference signal between patterns. Signals taken from the outside of the detector experience a reversed sign in comparison to signals taken from an inside portion of the detector. Several embodiments of the present invention utilize the reversed sign of the signal to increase the sensitivity of the apparatus. Experimental results and/or simulations suggest that a detector wired in a differential mode produces a larger signal upon detection of phase defects than a conventionally wired detector. For example, with first and second detector portions equal in area, the intensity of the resulting signal taken in differential mode has been found to be nearly 4 times the intensity of a signal taken in a standard or summing mode from the two detector portions. This results in an increase in the effect of the defect upon an output image, i.e. this technique is more sensitive to defects.

Processing of the separate signals generated by the separate regions or portions of the detector 314 is handled by analyzer 316. In one embodiment, the analyzer 316 comprises a summing amplifier which converts one of the detector signals to its negative value and thus provides a resulting differential signal. In another embodiment, the separate signals from the detector portions are summed to produce a resulting signal equivalent to signals obtained from the full detector using conventional scanning optical microscopy systems to identify defects, such as pattern defects as illustrated by defect 108 in FIG. 1B. Analyzer 316 may comprise a processor with appropriate connective circuitry well known to those of skill in the art or may include a simple summing circuit without a connected processor. Alternatively, the analyzer 316 for analyzing detected signals and the controller 308 for initiating detection may be integrated in a single device comprising any suitable combination of software and hardware. It is to be understood that the invention is not limited in its application to the details of construction or arrangement of analyzing components described or illustrated but extends to all configurations wherein the detector signals may be processed in accordance with the descriptions provided herein.

Figure 4A:
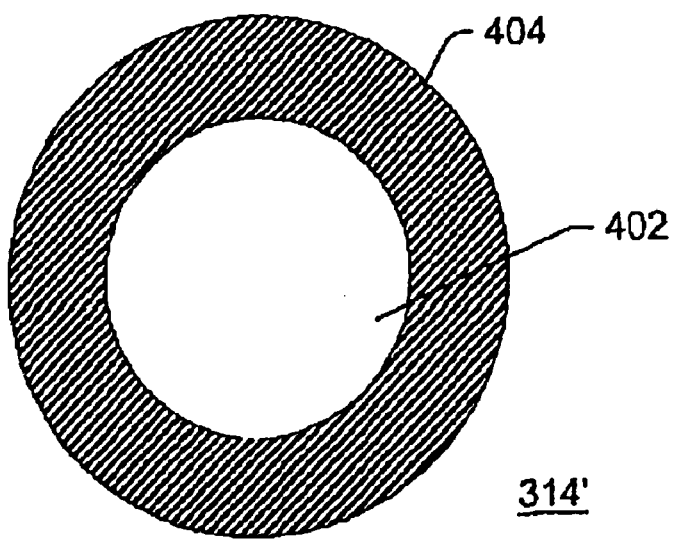
FIGS. 4A, 4B and 4C depict top views of a split detector in accordance with embodiments of the present invention.
Figure 4B:
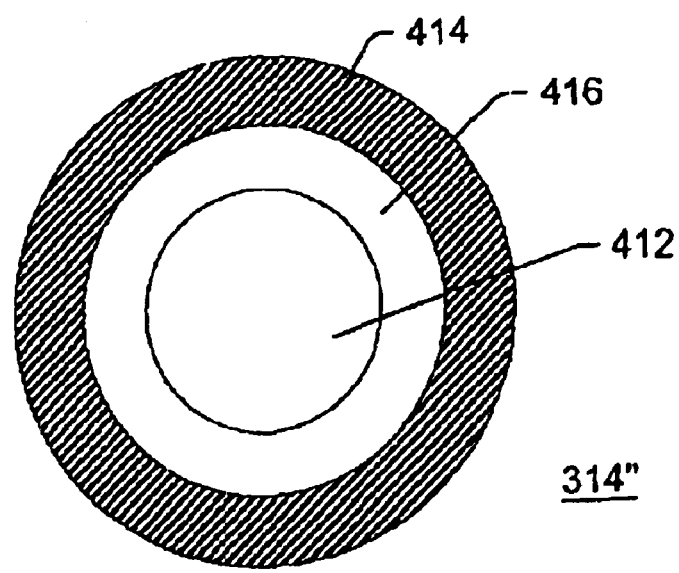

FIGS. 4A and 4B depict top views of a first and second embodiment, respectively, of detector 314 in accordance with the first group of detector embodiments. That is, configurations of example detectors preferably used with defocusing are shown. In the first embodiment shown in FIG. 4A the detector 314' is divided into a first portion 402 and a second portion 404. In a specific embodiment, first portion 402 comprises a circular region and second portion 404 comprises a contiguous annular region. The first and second portions are concentric ideally about the centerline of the light waves collected by collector 312. In a specific embodiment, first portion 402 and second portion 404 are equal in area. This may be accomplished, for example, in using the circular and annular portions described by setting the outer diameter of the circular first portion 402 to be equal to about 0.7 times the outer diameter of the annular second portion 404. Each of the portions therefore represents a portion of the detector corresponding to a smaller range of angles, i.e., a lower sigma value.

The embodiments of the present invention achieve improved sensitivity by using a detector split into at least two zones and by combining those signals from the separate zones in a differential manner. Suitable results have been obtained when the detection and the subsequent processing of the signals by the analyzer have been applied to defocused light beams. While not wishing to be bound by any theory, it is believed that the mechanisms involved in producing the larger signal using defocusing are based on the complex amplitudes of the optical field. Phase information imaging is described in greater detail in "Fourier Imaging of Phase Information in Scanning and Conventional Optical Microscopes", C. J. R. Sheppard and T. Wilson, Philosophical Trans. of the Royal Society of London, Vol. 295, A1415, February, 1980, pp. 513–536, which is incorporated fully by reference for all purposes.

In focused images direct phase information is lost when the detector converts the complex amplitude A of the optical field to an electrical intensity AA. The optical transfer function at focus is real so for all phase shift objects the image intensity at the site of the phase defect is nearly the same as it would be in the case of no phase defect being present, provided the illumination is on axis. In defocused images the transfer function has an imaginary part. As a result of this out of phase, imaginary part of the focused beam, the contrast of phase defects is greatly increased when defocus is coupled with a low sigma. Alternatively, as described below with respect to the second group of embodiments, rather than using defocus, off axis illumination can be used to enhance phase sensitivity. Detectors that are split into portions such that the centroid of the detector is off axis are equivalent to illumination systems in conventional microscopes that are off axis. Off axis illumination is another way to enhance phase contrast by mixing in signal components that shift the phase defect signal so that a portion of this signal is in phase with respect to the background signal.

Light scattered from most small phase defects is in quadrature to the unscattered light. This is undesirable, as a small signal in quadrature to the unscattered signal will only appear to second order in the detected signal. That is, if epsilon represent the strength of the amplitude scattering of the phase defect normalized to the amplitude of the unscattered plane wave, and the absolute value of epsilon is small compared to 1, then the image modulation due to the defect responds in proportion to (epsilon)$^2$. Zernike phase plates and defocus are commonly used to improve phase defect visibility by getting the defect signal to add linearly, not in quadrature, to the unscattered signal, so that the defect modulation is proportional to epsilon, rather than (epsilon)$^2$, and thus produces a higher amplitude signal. Using off axis illumination is yet another way of achieving phase sensitivity, without needing to defocus the image.

In an alternate embodiment, shown in FIG. 4B, detector 314" is shown with three zones, a first portion 412, a second portion 414, and a third portion 416 separating the first portion 412 from the second portion 414. In this instance, the third portion 416 represents a "dead" band, i.e., an annular isolation region. None of the light detected by this portion is used to generate an output signal. Various diameters of the first, second, and third portions will produce suitable results. For example, a diameter of the first portion 412 of 0.3 times the outer diameter of the second portion 414, and the outer diameter of the third portion 416 equal to 0.8 times the outer diameter of the second portion 414 works well. Outer diameters of the first portion from 0.3 to 0.8, and the second portion having an inner radius from 0.3 to 0.9 work well.

Figure 4C:
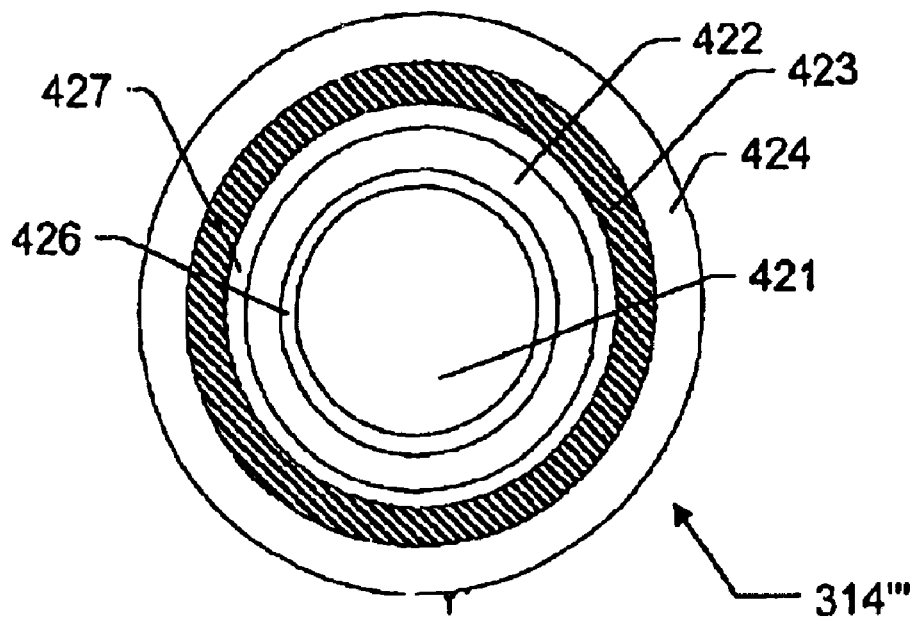

In other embodiments, the detector may comprise any additional number of portions, such as, for example, a third portion and a fourth portion. FIG. 4C depicts a top view of a split detector 314'" having four portions or zones. In one embodiment, the signals generated from a first portion 421 and a third portion 422 may be summed and the signals from a second portion 423 and a fourth portion 424 may also be summed. The resulting summed signals may then be subtracted to provide a difference signal for analysis. In other embodiments, two inner zones (i.e., a selective combination of the detector portions) may be selected from a detector having three or more portions so as to selectively produce a detector signal corresponding to an inspection/collection lens system having a low sigma value. This allows use of a detector which, by virtue of the multiple detector portions, may present different sensitivities for different applications by varying the sigma value. In another embodiment, "active" portions of the detector, i.e., the portions providing a detector signal for further analysis, may be separated by isolation regions (426, 427) or "dead" zones to minimize interference generated in signals in the active portions of the detector. Though in some cases the isolation regions may approximate the active regions in size, the invention is not so limited. The size of the isolation regions may be minimized or in some embodiments the isolation regions may be eliminated and still be within the scope of the present invention. The present invention is not limited to using all of the available zones in the detector to generate a signal, and, as illustrated above, is not limited to selecting contiguous zones for generation of a summed signal. Specific zones or portions may be "dead" zones and the zones selected for summing may be contiguous or not, selected in accordance with the sensitivity desired.

Another advantage to having multiple annular detector segments is that it allows for flexible operation with different pixel sizes. For instance, larger pixels are used at times for mask inspection. This is accomplished by reducing the NA of the objective lens. Since the sigma of the imaging system is given by the ratio of the sine of the collection angle to the sine of NA, changing NA for different pixel sizes requires changing the sine of the collection angle if sigma is to remain the same. If sigma were allowed to increase, as it would if the NA were reduced and no change were made in the detector configuration, the microscope's phase sensitivity would decrease. One way to do this is to have a detector with multiple annular regions so that when the NA is reduced elements closer to the center can be used, thus keeping sigma constant with varying pixel size.

In another embodiment, a Zernike phase shift plate or similar phase plate is introduced in the pupil plane to improve phase sensitivity in lieu of defocusing. Zernike techniques provide a mechanism for emphasizing small phase steps.

Figure 5:
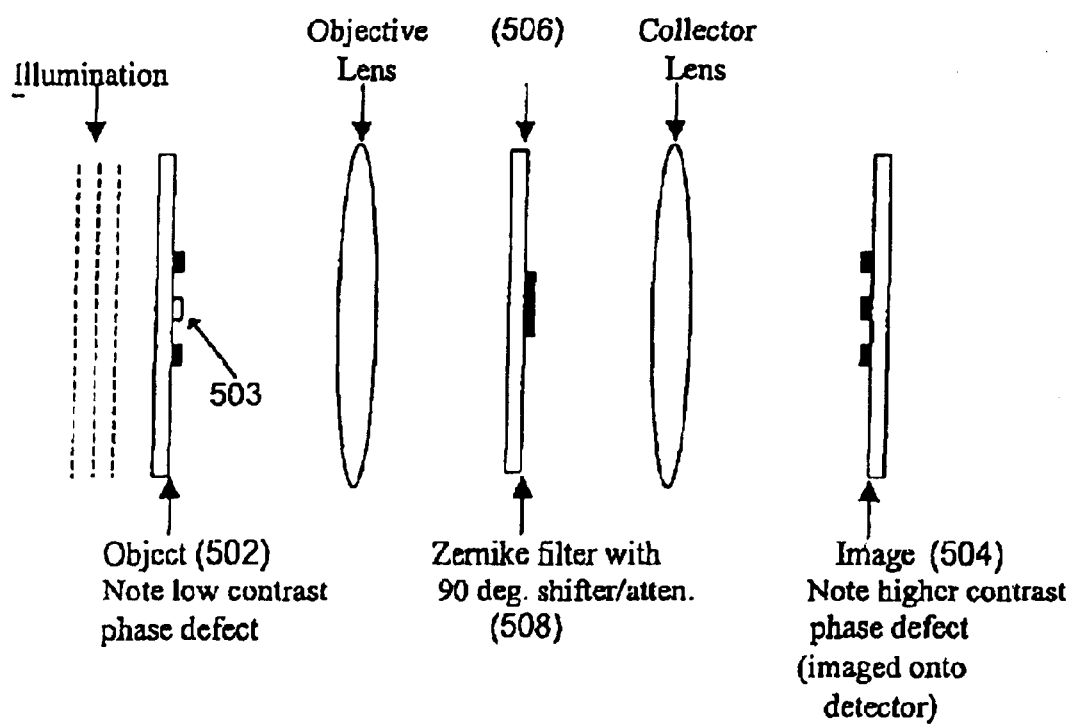
FIG. 5 is a diagrammatic representation of a conventional optical microscopy system utilizing a Zernike plate.

At the left of FIG. 5 an object 502 having a low contrast phase defect 503 is illuminated, and at the right a phase contrast image 504 of this object is produced. The phase contrast image 504 is produced by forming an intermediate Fourier plane 506 of the image and inserting a Zernike phase contrast filter 508 in this plane. This filter 508 shifts the amplitudes of the low spatial frequency components of the image 504, which forms the background of the image 504, by 90 degrees. It may also attenuate the low spatial frequency components of the image 504 as well, which has the effect of reducing the overall brightness of the image but increasing the contrast of phase defects in the image, which is sometimes desirable. The phase contrast is increased by this filter 508 because when the output image is formed from this filtered Fourier plane 506 the background is now collinear in amplitude with the components of the image due to the phase defect. Therefore the signals add linearly rather than in quadrature. For instance, a small phase defect that is 0.1 of the amplitude of the background that is imaged using a phase contrast technique would give an approximately 10% modulation of the image at the point of the defect. However, if this amplitude were in quadrature rather than in phase it would only give approximately a 1% modulation of the image, which would make it much harder to detect.

A defocused imaging system is somewhat like a focused system with a (Zernike) phase plate where the phase shift increases quadratically with spatial frequency (or pupil radius). A Zernike plate or a complex amplitude plate may be used to produce a phase shift between the regions of the detector, such as between the annular and central regions. Zernike plates usually specify a 90 degree phase shift and usually are attenuating for the direct light (or zero order). Those skilled in the art with the benefit of this specification would recognize that complex amplitude plates may be selected to produce variations in both phase and amplitude to meet a desired sensitivity.

Typically, the signals generated from the analyzer are connected to a display generator 318 (see FIG. 3) in order to create a display of the inspected mask. The display generator may comprise a CRT, an LCD screen, or other suitable display device coupled with appropriate processing circuitry to convert the resulting voltage signals received as the light beam scans the mask to an image on the display screen of the display generator 318. Generally, a phase defect image derived from an inspected mask will show edges of layers in addition to phase defects. For example, a difference image may be obtained from two identical areas of the mask to isolate the images generated by the phase defects. If the difference image contains pixel values above a certain threshold, then a defect has been identified. This threshold is set so that defects above a certain specified size are found reliably, while the number of false and/or nuisance defects is kept acceptably low.

In one embodiment, the techniques of the present invention permit pattern defect inspections and phase shift inspections to proceed using a single scanning optical microscopy system in two passes. The number of passes depends on the algorithms, noise, and desired defect sensitivities. The dual pass system may be used with both the first group of embodiments and the second group of embodiments. That is, the dual pass inspection may be performed using the annular segmented detector with defocus coupled with a second pass having a focused signal. Alternatively, the pattern defect inspections may be implemented with the second group of embodiments without the need for changing the level of focus of the inspection beam.

Figure 6:
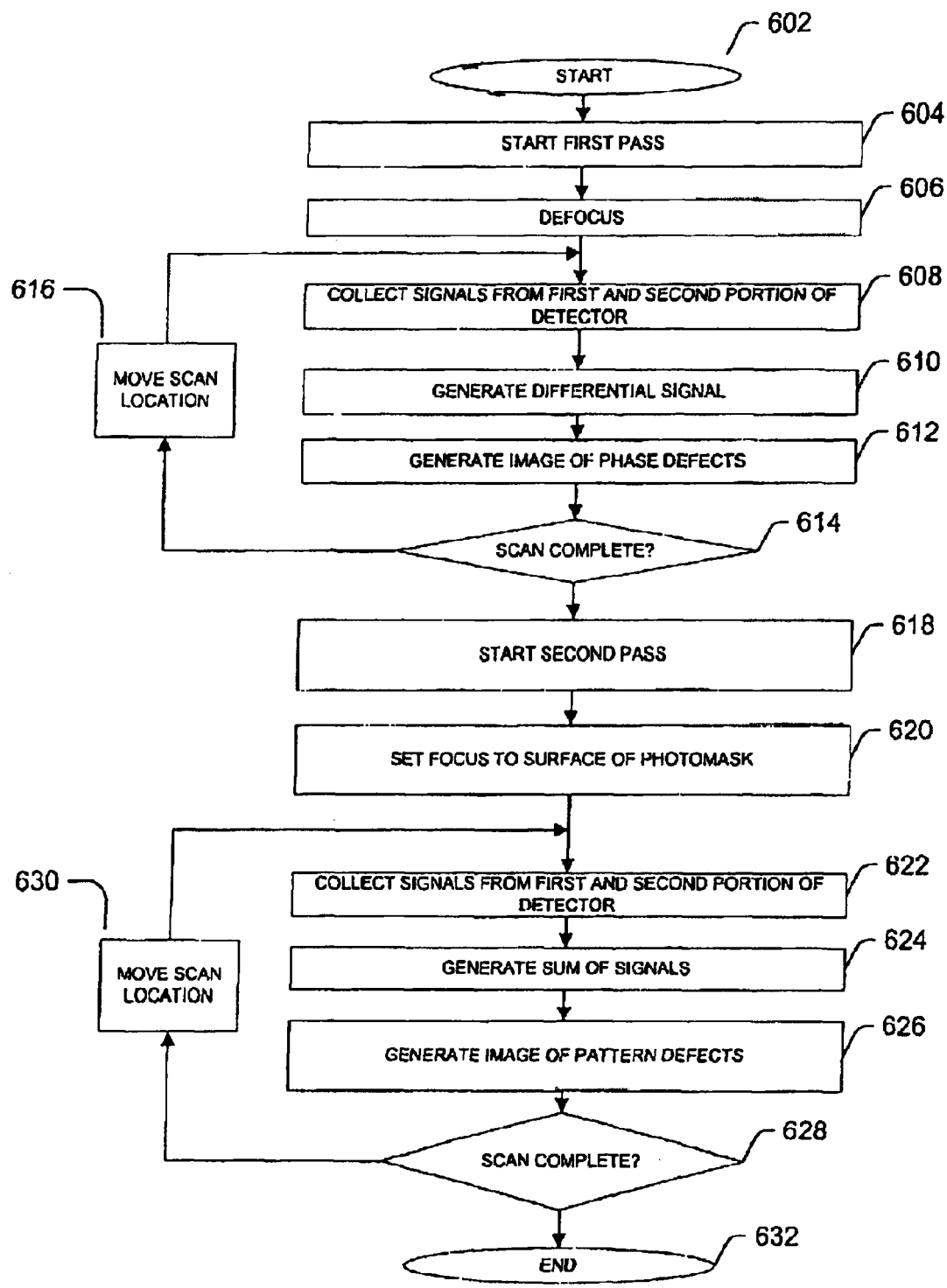
FIG. 6 is a flowchart illustrating a procedure for inspecting phase shift defects and pattern defects in accordance with one embodiment of the present invention.

FIG. 6 is a flowchart illustrating an inspection technique for phase shift defects and for pattern defects in accordance with one embodiment of the present invention. In general terms, the system completes pattern and phase defect inspections in two passes over the photomask to be inspected. The first pass commences with an inspection for phase defects in the photomask (604). Phase defect inspection, in accordance with several embodiments, requires a defocused image. The focus is set to a predetermined distance in one direction from the surface of the photomask (606). Suitable distances will vary as a function of the wavelength ($\lambda$) of the impinging light waves and numerical aperture (NA) of the objective lens, specifically in proportion to $\lambda/NA^2$. For example, a suitable range lies from a distance 0.5 to $3*\lambda/NA^2$. Suitable results have been obtained in the range from about 200 nm to about 500 nm but these values may vary according to the factors as discussed above. The scan commences with the incident light directed to a spot on the photomask and the collection of the resulting signals from a first and second portion of the detector (608). In this first mode, a differential signal is generated from separate portions of the detector (610). Subsequently, the resulting signal is used to generate an image of the mask to identify defects (612). A bright or dark picture element will be generated to correspond to the scanned spot. If the scan of the photomask is not complete (614), the scanning continues over the next section of the photomask (616). Various mechanisms may be used to perform the scanning as is known to those of skill in the art. For example, in one embodiment, the light is focused on a spot followed by the generation of detector signals. In order to perform the two-dimensional scan, the photomask may be moved in one direction and the beam moved in a direction perpendicular to the mask movement.

Once the scanning of the photomask for phase defects is complete, the second pass commences (618). Initially, in this conventional inspection mode, the focus is set to the surface of the photomask (620). This location is in fact typically set to the surface of the chrome layers patterned on top of the quartz layer of the photomask. In this mode, the signals are collected from the full detector by generating the sum of signals from the separate portions of the detector (622 and 624). As with the case of the phase defect inspection, the resulting signal is used to generate a picture element of an image displaying pattern defects (626). Scanning of the mask continues for pattern defects if the image is not complete (628, 630). Although this embodiment is shown commencing with an inspection for phase defects in a first mode followed by an inspection for pattern defects in a second mode, it will be recognized by those skilled in the art that the order of inspections may easily be interchanged without departing from the basic principles of the invention.

Figure 7:
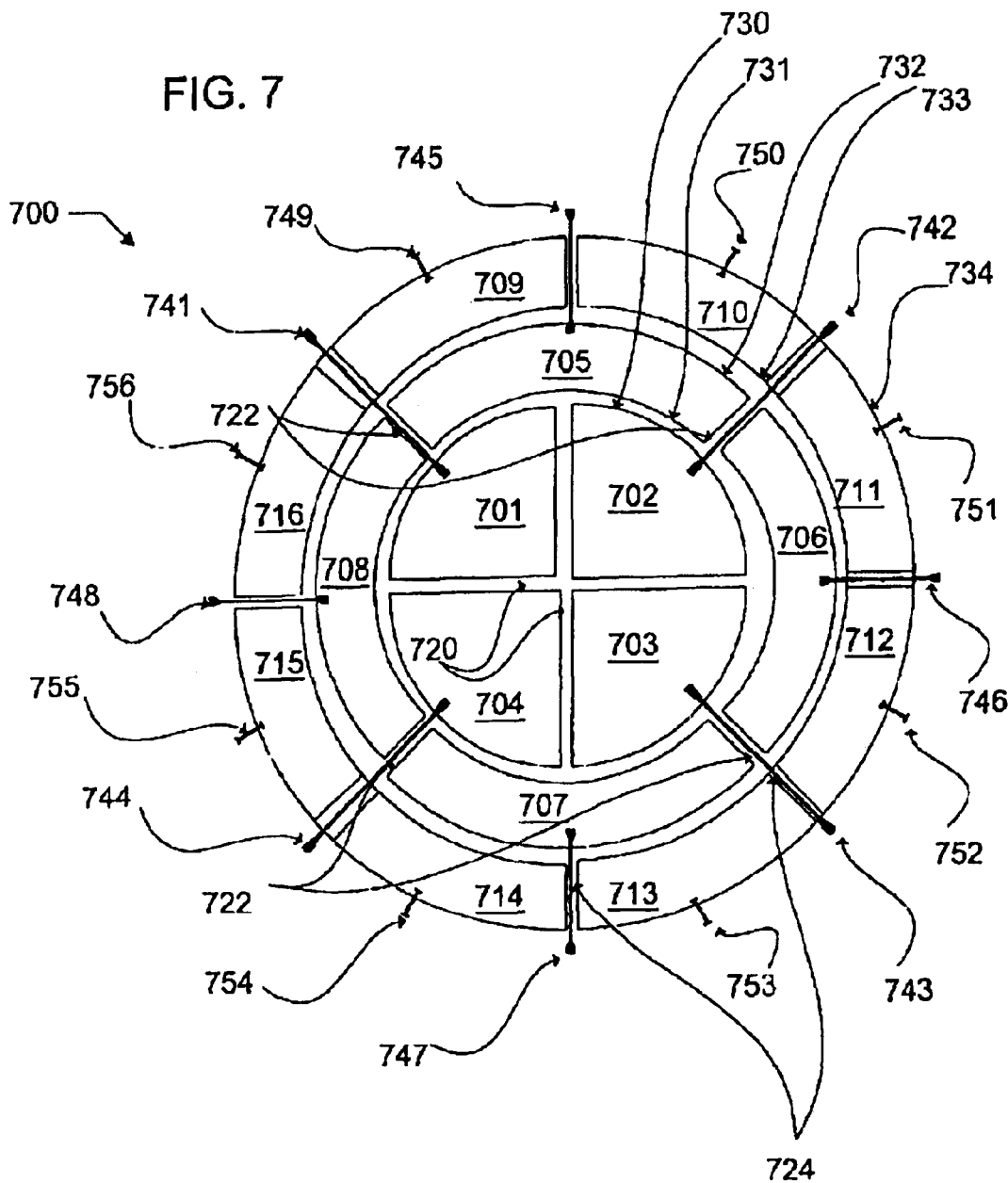
FIG. 7 is a diagram illustrating a segmented ring detector 700 in accordance with one embodiment of the present invention.

According to an alternative embodiment, the pattern defect inspection may take place in conjunction with phase defect inspection using a detector configured for off axis detection such as, for example, the detector illustrated in FIG. 7. According to the detectors and methods described with respect to the second group of embodiments (i.e., off-axis detection and/or illumination), phase defect detection occurs without the need for defocusing. Accordingly, the dual pass inspection may take place without the defocusing step described in step 606, said step replaced with a focusing step, i.e., focusing the inspection beam on the sample to be inspected. Moreover, dual focusing steps may not be needed. That is, focusing, for example to the surface of the photomask, will be needed in only the first of the passes. By combining phase defect inspection with pattern defect inspection in accordance with this alternative embodiment, the summed signals from the segments of the detector will produce an in focus conventional image without requiring a second focusing step. In yet another alternative embodiment as will be described further below, images may be formed at the same time (i.e., in the same scanning pass) that are both summed and differenced images. The summed images will correspond to conventional defect inspection using a conventional detector.

FIG. 7 is a diagram illustrating a segmented ring detector 700 suitable for providing increased phase sensitive signals near pattern edges, in accordance with a specific embodiment of the second group of embodiments of the present invention. As illustrated, the inner circular region of the segmented ring detector 700 is segmented into quadrants 701–704. A first annular region surrounding the inner circle is segmented into regions 705–708. A second annular region surrounding the first annular ring is segmented into eight regions, 709–716. Segments may be selected to provide increased phase sensitivity to phase shift mask defects as compared to conventional detectors. The differential signal is obtained by providing at least two channels from the detector outputs. A differential signal is obtained by selecting individual elements from the multiple elements of the segmented ring detector 700 to correspond to each of the channels. The detector elements for each of the inner circular region, the first annular region, and the second annular region are preferably arranged in a radially symmetric manner.

The detector 700 includes signal wires 741–756, preferably arranged in the embodiment shown to have relatively equal capacitances. In the configuration shown, the detector elements in the first annular region (i.e., 705–708) are arranged in a radially symmetrical configuration about the center of the detector, with the gaps 722 between the elements of the first annular region offset from the gaps 720 between the quadrant elements (701–704) of the inner circular region. Likewise, alternate ones of the gaps 724 between the eight elements of the second annular region (i.e., elements 709–716) are offset from the first annular region gaps 720 so as to permit conductive traces to connect to the detector elements of the second annular region as shown. The gaps between the detector elements (e.g., 720, 722, 724) may be any suitable size which does not significantly affect the areas of the detector elements, i.e. the active portion of the detector. Gaps of 0.1 mm are expected to work well. The present invention may be implemented with any suitable signal wires connected to various segments of the detector, however configured. Any detector material and insulation material providing sufficient isolation between the detector element signals may be used, as known by those skilled in the art.

In accordance with one embodiment of the present invention, the signal traces from the individual detector elements are connected to preamplifiers. After preamplification, the signal levels may be combined in accordance with programmed logic implemented in an analyzer, such as may be contained in a microprocessor, general purpose computer, FPGA, or any other suitable programmable device. Such programming may be performed, for example, in an analyzer 316 such as illustrated and described with reference to FIG. 3. An example embodiment of such programming control is described in further detail with respect to FIGS. 9A and 9B below.

Detector elements from the multiple element detector may be combined to optimize the sensitivity levels to phase mask defects, particularly those located in etched portions in proximity to the edges of the opaque (chrome) patterns. The analyzer may be configured so that the elements are programmably selected. That is, signals from different elements are selected and combined to correspond to the type of defects expected to be encountered and the orientations of the patterns near the defects. As noted above, combining elements from all detector elements provides a signal output equivalent to the output signal from a conventional detector in a binary mask inspection system.

Detector elements are selected so that differential signals provide a satisfactory sensitivity level in light of the configuration of the chrome patterns on the mask. For example, differential signals between the top and bottom elements of the detector may be selected in the presence of horizontal chrome edges. Differential signals between the left and right elements of the detector (i.e., those appearing in the left and right hemispheres of the detector) may be selected in the presence of vertical chrome patterns on the phase shift mask. As a further example, detector elements in a diagonal configuration, i.e., those appearing on either side of a diagonal line roughly parallel to a diagonal line in the pattern may be used to detect phase defects near the diagonal pattern line.

For example, the differential signal may be generated by summing detector elements 701 and 702 and separately summing detector elements 703 and 704, then using the two summed channels to provide the differential signal. On-edge phase defects near vertical pattern lines could also be detected more easily by selecting the detector elements so that the differential signal is generated between the left and right elements of the detector, for example, by comparing the summed signal from elements 701 and 704 with the summed signal from elements 702 and 703. While not wishing to be bound by any theory, it is believed that proper selection of the elements increases sensitivity (i.e., greater contrast) by permitting light transmitted through the phase defect to be mixed with light from adequate portions of the surrounding non-defective quartz areas. Without intending to be limited to any theory it is believed that since using a detector with an off axis centroid is equivalent to using off axis illumination in a conventional imaging microscope, the off axis illumination serves to provide a reference signal whose phase varies linearly across the field. Since this reference phase is not flat, it is no longer the case that the signal from the phase defect will be in quadrature to the reference signal at all points. Isolated phase defects imaged with off axis illumination tend to show up as small bipolar modulations. That is, an isolated phase defect will show up in the inspection image as a bright spot next to a dark spot. Phase defects near a chrome-glass edge have a similar character, though the interaction of the phase defect signal with the background is more complex in this case since the background signal is not uniform near an edge.

Although all detector elements may be processed in parallel, including deriving a resultant differential signal, substantial image processing computer and memory resources may be saved by combining signals from detector elements prior to processing. Rather than processing 16 or more different channels, the detector elements may be selectively combined to produce a minimum of two channels, with a differential signal obtained between the two channels.

In one embodiment, images are formed at the same time that are summed and differenced images. Summing the images from the detectors produces an image that could be used to find conventional binary defects, whereas the difference images would be better suited to finding phase defects. That is, by summing the detectors using this configuration, a sharp, in-focus image may be obtained that is equivalent to the detector image obtained using a conventional single element detector.

The examples are intended to be illustrative and not limiting. The invention is intended to cover all combinations and permutations of elements selected to provide the desired sensitivity. For example, the invention is intended to cover all combinations of elements, such as for example, elements 701, 702, 705, 709, 710, 711, and 716 for the sum of signals from the upper half of the detector.

The segmented ring detector or multiple element detector may be configured in many alternative ways without departing from the spirit and scope of the present invention. As a further example, the multiple element detector may be formed from a circular central region such as constituting the detector elements 701–704 formed within diameter 730 as illustrated in FIG. 7. The multiple element detector used in embodiments of the present invention may be formed with or without the detector elements illustrated in the first annular region (elements 705–708) or the second annular region (elements 709–716). Moreover, the number of detector elements within a particular central region, annular region, or band may vary without departing from the scope of the invention. For example, although the second annular region is depicted in FIG. 7 as containing 8 detector elements, the invention is intended to cover configurations having no second annular region, as little as 2 detector elements in the annular region, or any number of detector elements in the annular region. Moreover, the detector elements need not be arranged in a circular or annular region. The detector may be in any general two-dimensional shape, such as rectangular with rectangular or any other shaped elements or segments. Although in a specific embodiment, the detector elements are arranged in a radially symmetric manner, the scope of the present invention is also not so limited. For example, the detector may be configured so that it is segmented into at least 4 elements and the elements configured to form a Cartesian grid pattern. Alternatively, the elements may be configured to form a polar grid pattern. For a further example, the multiple element detector may be configured in a manner biased towards a predominate pattern configuration on the photomask, such as by having more elements in a up-down direction to provide greater flexibility for slight angular changes of predominately horizontal pattern lines.

It should be noted that the segmented ring detector 700 illustrated in FIG. 7 is drawn for illustration purposes and is not to scale. The sizes and configurations of the detector elements may be one of a wide variety of dimensions. For the configuration illustrated in FIG. 7, and with an image formed on the detector of the area to be inspected comprising an area of about 4.5 mm in diameter, the following diameters for the detector sections, while not intended to be limiting, have been shown to be suitable: diameter 730=2.0 mm; diameter 731=2.2 mm; diameter 732=3.0 mm; diameter 733=3.2 mm; and diameter 734=4.5 mm.

The techniques and systems of the embodiments of the present invention are expected to provide high image contrast for phase defects, particular in those defects located near chrome edges, in comparison to other phase contrast techniques. The semiconductor industry will likely rely more and more on alternating phase shift mask technologies to print future generations of devices, particularly when the development of shorter wavelength lithography technologies lags behind industry expectations. Thus, the systems and methods of the present invention provide critical inspection capabilities in the form of increased sensitivity to defects in alternating PSM photomasks.

The inspection system and methods described may also be implemented in any illumination imaging system suitably configured to generate the illumination from at least four sources, or, equivalently, four different apertures in four different locations. In such a system apertures are configured in the illumination path to illuminate the object from different directions. In one embodiment, at least four different apertures in four different locations are used. The images obtained from each aperture are obtained sequentially.

Figure 8:
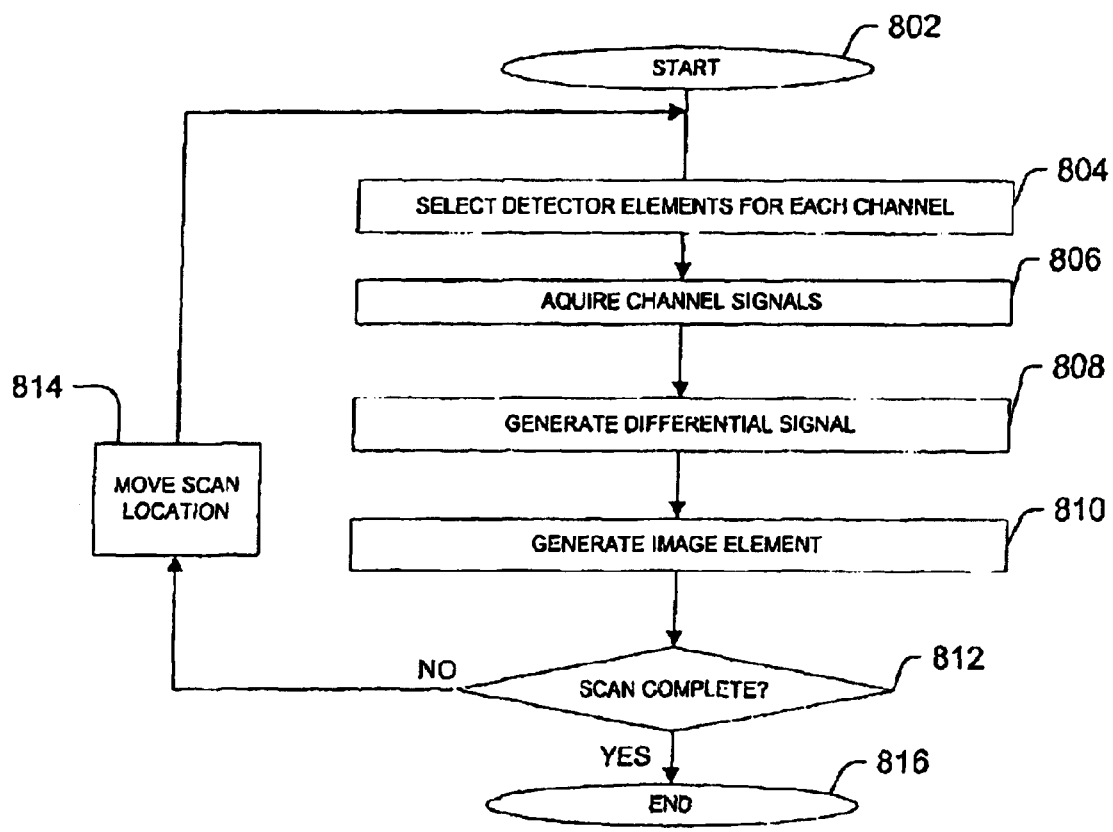
FIG. 8 is a flowchart illustrating a technique for inspecting phase shift mask defects in accordance with one embodiment of the present invention.

FIG. 8 is a flowchart illustrating a technique for inspecting phase shift mask defects in accordance with one embodiment of the present invention. This technique is generally applicable to the embodiments of the second group, i.e., the detector using the off-axis differential detection techniques and with segmented detectors such as of the type illustrated, for example, in FIG. 7. Initially the process starts at an operation 802 with a first selected scan location and an appropriate focus setting. A suitable focus setting is expected to be focused on the mask surface or at a defocused level. Generally, a focus setting within + or −2 depths of field will produce suitable results. Preferably the focus setting will lie within + or $-\lambda/NA^2$, where $\lambda$ is the wavelength of the inspection source illumination. For example, $\lambda$ for an I Line laser is 364 nm, whereas the NA in such a system typically lies in the range of 0.6 to 0.85. Defect signal measurements using configurations of the multiple element or segmented ring detectors of the present invention are expected to change slowly with defocus. In comparison, other phase contrast techniques are expected to exhibit greater sensitivity as a function of the amount of defocus.

Next, in an operation 804, programming of the detector is performed. In one embodiment, detector elements are selected for each of the channels in accordance with the types of defects determined by image processing techniques such as edge detection. In accordance with one embodiment of the present invention, two detector channels are selected. As discussed, elements from the top and bottom of the detector may be separately summed to provide a differential signal. Alternatively, other configurations of elements from portions of the detector may be separately summed to generate the differential signal. The techniques of the embodiment are intended to cover all combinations and permutations using the multiple detector elements, whether limited to two channels, or extended to include additional channels and more than one element for each channel. The signal lines may be connected from the detector elements to any suitable form of hardware and/or software to enable the selection and summing of individual detector elements and the subsequent image processing.

After the programming operation, the signals are collected from the selected detector portions to form each signal channel in an operation 806. While a minimum of two channels is needed to generate a differential signal, additional signal channels may be provided to the analyzer processing input. Using two channels or more, a resulting differential signal may be generated in an operation 808. As described above, the differential signal from a multiple element detector having 4 or more elements shows higher sensitivity than other phase contrast techniques to certain types and locations of phase defects. In an operation 810 an image element of the phase defects is generated.

In a next operation 812, a determination is made as to whether the scan is complete. If the scan is not complete, scanning continues (814) with operations 804 through 812 repeated. Thus, an image or image signal may be generated by storing and combining the individual image elements generated at each scan location. Typically, phase contrast imaging detects defects by comparing the signal from a mask portion to the signal from another identical mask portion, such as from a similar pattern on the same mask or from a stored image or rendered from a design database. Generally, the defect will be detectable using the difference images from the two patterns. Defect determination typically involves comparison of the tested area to a similar portion of the reticle (photomask) or rendered from a design database. For example, die-to-die or cell-to-cell comparisons may be made. In cell-to-cell comparisons, a repeating portion of the same pattern on a particular die is compared to the test area. In die-to-die comparisons, greater scan movement is required and more image storage is required in order generate a difference inspection image between the test area and the reference area, the latter located typically at a second die location on the photomask or wafer. For example, dies used in a die-to-die comparison may be 60 mm apart on a reticle.

In a preferred embodiment, image processing or other signal processing operations performed on images from the multiple element detector may be programmed to select the elements which ultimately may be used to generate the differential signal as based on the configuration of the opaque pattern in proximity to the scan spot. That is, selection of the detector elements may be programmed to be less sensitive to a pattern line edge effect at a particular scan location or locations. As the signal or image elements derived from the scan operations scan are processed (for example, by image processing techniques performed on the composite image), the selection of detector elements may respond to changes in location in the composite image. Edge detection techniques known in the relevant art are one example of techniques to assist in determining the detector element combinations to be selected for analysis. Although edge detection techniques have been described the present invention is not intended to be limited to such techniques. Any suitable technique may be used to process the composite signal or image to assist in determining the selection of the multiple detector elements to optimize or increase the sensitivity to specified defects, such as PSM defects appearing near chrome patterns, without departing from the scope of the invention.

Any suitable method may be used to connect the multiple detector elements to an image processor. For example, the segmented ring detector configuration illustrated in FIG. 7 enables signal lines to be connected to each of the multiple elements while maintaining equal capacitance values for each of the lines.

Various mechanisms may be used to perform the scanning as is known to those of skill in the art. For example, in one embodiment, the light is focused on a spot followed by the generation of detector signals. In order to perform the two-dimensional scan, a stage holding the photomask or other sample may be moved in one direction and the optical inspection beam moved in a direction perpendicular to the mask movement by a controller, such as controller 308 illustrate in FIG. 3.

Although the embodiments of the present invention have been described by providing examples in the context of a semiconductor photomask, the invention is not so limited. The scope of the invention is intended to encompass all forms of defect inspection in semiconductor processing, such as including defects appearing on semiconductor wafers and comparisons between dies. Accordingly, the descriptions and illustrations provided herein are intended to be exemplary and not limiting.

By configuring the detector to provide off-axis signals as described herein, images of the inspection surface may be formed that have a preferred direction, i.e., anisotropic images. Thus, according to the methods described, the sensitivity may be increased in one direction. This is advantageous in inspecting small defects, such as phase shift defects, appearing adjacent to pattern lines. By segmenting the detector as described, improved phase defect sensitivity may be obtained. Moreover, since the off-axis detection may be operated at or near focus, summing the signals from the separate detector elements provides the equivalent to a conventional detector image.

Figure 9A:
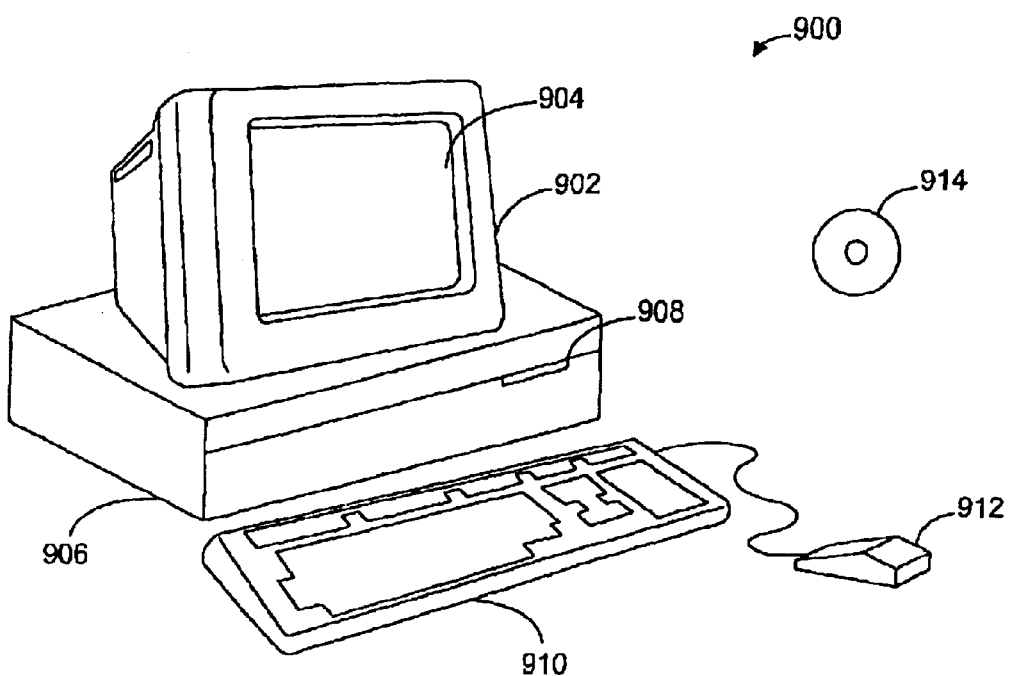
FIGS. 9A and 9B illustrate a computer system 900 suitable for implementing embodiments of the present invention.
Figure 9B:
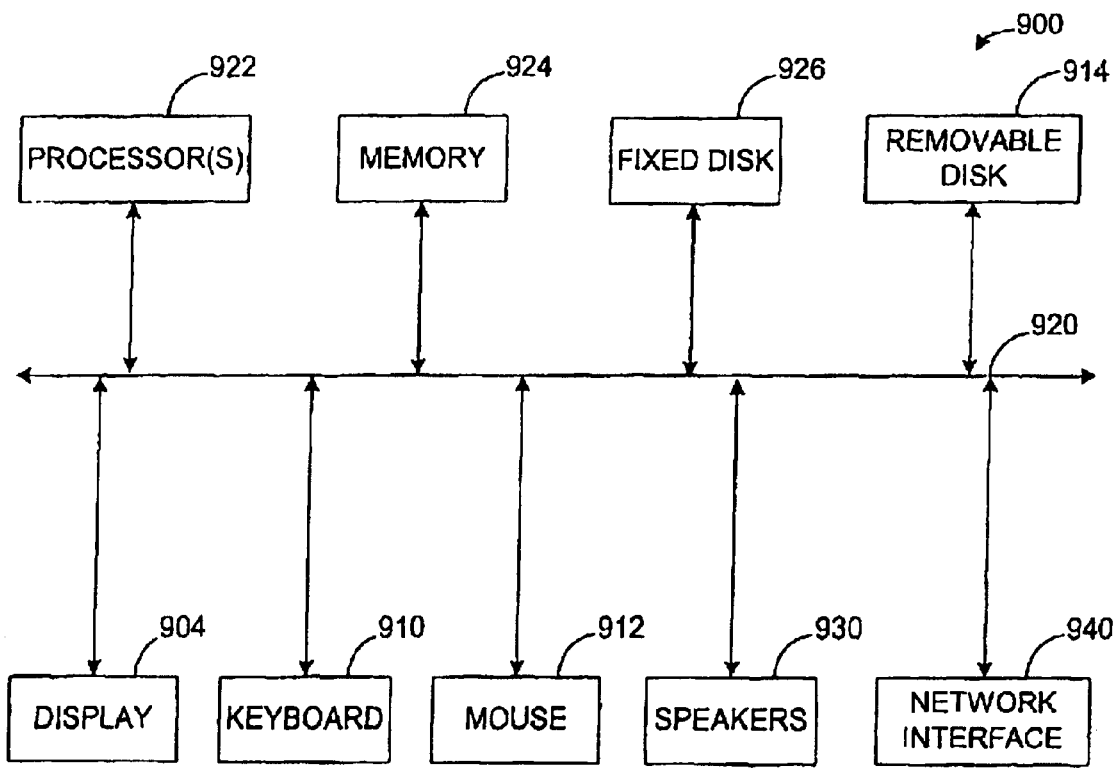

FIGS. 9A and 9B illustrate a computer system 900 suitable for implementing embodiments of the present invention. For example, the computer system 900 may be configured or programmed to control various operating parameters of a scanning optical microscopy system, such as including stage movement or scan movement. The computer system 900 may be configured to perform both the control and analyzer functions as described earlier with reference to FIG. 3. Additionally, the software may be configured to perform selection of the detector elements for the generation of image signals, as well as the image processing involved in determining whether the image signals identify phase defects. The computer system 900 may also direct other metrology and inspection procedures, including performing a standard scan using all elements of the multiple element detector.

FIG. 9A shows one possible physical form of the computer system. Of course, the computer system may have many physical forms ranging from an integrated circuit, a printed circuit board and a small handheld device up to a huge super computer. Computer system 900 includes a monitor 902, a display 904, a housing 906, a disk drive 908, a keyboard 910 and a mouse 912. Disk 914 is a computer-readable medium used to transfer data to and from computer system 900.

FIG. 9B is an example of a block diagram for computer system 900. Attached to system bus 920 are a wide variety of subsystems. Processor(s) 922 (also referred to as central processing units, or CPUs) are coupled to storage devices including memory 924. Memory 924 includes random access memory (RAM) and read-only memory (ROM). As is well known in the art, ROM acts to transfer data and instructions uni-directionally to the CPU and RAM is used typically to transfer data and instructions in a bi-directional manner. Both of these types of memories may include any suitable computer-readable media described below. A fixed disk 926 is also coupled bi-directionally to CPU 922; it provides additional data storage capacity and may also include any of the computer-readable media described below. Fixed disk 926 may be used to store programs, data and the like and is typically a secondary storage medium (such as a hard disk) that is slower than primary storage. It will be appreciated that the information retained within fixed disk 926, may, in appropriate cases, be incorporated in standard fashion as virtual memory in memory 924. Removable disk 914 may take the form of any of the computer-readable media described below.

CPU 922 is also coupled to a variety of input/output devices such as display 904, keyboard 910, mouse 912 and speakers 930. In general, an input/output device may be any of: video displays, track balls, mice, keyboards, microphones, touch-sensitive displays, transducer card readers, magnetic or paper tape readers, tablets, styluses, voice or handwriting recognizers, biometrics readers, or other computers. CPU 922 optionally may be coupled to another computer or telecommunications network using network interface 940. With such a network interface, it is contemplated that the CPU might receive information from the network, or might output information to the network in the course of performing the above-described method steps. Furthermore, method embodiments of the present invention may execute solely upon CPU 922 or may execute over a network such as the Internet in conjunction with a remote CPU that shares a portion of the processing.

In addition, embodiments of the present invention further relate to computer storage products with a computer-readable medium that have computer code thereon for performing various computer-implemented operations. The media and computer code may be those specially designed and constructed for the purposes of the present invention, or they may be of the kind well known and available to those having skill in the computer software arts. Examples of computer-readable media include, but are not limited to: magnetic media such as hard disks, floppy disks, and magnetic tape; optical media such as CD-ROMs and holographic devices; magneto-optical media such as floptical disks; and hardware devices that are specially configured to store and execute program code, such as application-specific integrated circuits (ASICs), programmable logic devices (PLDs) and ROM and RAM devices. Examples of computer code include machine code, such as produced by a compiler, and files containing higher level code that are executed by a computer using an interpreter.

Although the foregoing invention has been described in some detail for purposes of clarity of understanding, it will be apparent that certain changes and modifications may be practiced within the scope of the appended claims. It should be noted that there are many alternative ways of implementing both the method and apparatus of the present invention. Accordingly, the present embodiments are to be considered as illustrative and not restrictive, and the invention is not to be limited to the details given herein, but may be modified within the scope and equivalents of the appended claims.

What is claimed is:

1. A method for detecting phase defects in a semiconductor processing photomask or wafer, the method comprising:
    collecting a light beam reflected from or transmitted through the semiconductor processing photomask or wafer at a detector comprising at least four elements;
    selecting at least a first element of the at least four elements and at least a second element of the at least four elements to generate respectively a first signal and a second signal, wherein the first element and the second element are selected to correspond to the orientation of opaque pattern lines on the photomask in the proximity of the first light beam location on the photomask; and
    obtaining the difference between the first signal and the second signal to produce a resulting signal indicating whether there is a defect present.

2. The method recited in claim 1 wherein the detector is configured to provide a signal corresponding to the light collected at any selected one of the quadrants of the detector isolated from the light collected from the other 3 quadrants.

3. The method recited in claim 1 wherein the at least four elements are configured in a Cartesian grid pattern.

4. The method recited in claim 1 wherein the at least four elements are configured in a polar grid pattern.

5. The method recited in claim 1 wherein the at least a first element comprises a first element and a third element and the at least a second element comprises a second element and a fourth element.

6. The method recited in claim 1 further comprising moving the light beam to a second location on the photomask and repeating the steps of claim 1 in accordance with the state of the programmed logic.

7. The method recited in claim 1 further comprising repeating the operations of claim 1 for a plurality of locations on the photomask or wafer to generate an image signal and comparing the image signal to a similar pattern location on one of a same die on the photmask or wafer, another die on the photomask or wafer, or a pattern from a design database to identify defects.

8. The method for detecting phase defects in a semiconductor processing photomask or wafer in a first mode recited in claim 1, the method further comprising in a second mode:
    collecting a light beam reflected from or transmitted through the semiconductor processing photomask or wafer at a detector comprising at least four elements; and
    selecting each of the at least four elements and summing the signals to generate a resulting signal indicating whether there is a defect present.

9. The method recited in claim 1 wherein the detector comprises a central region having at least 4 elements.

10. The method recited in claim 9 wherein the central region comprises a circular region about the center of the detector.

11. The method recited in claim 1 wherein the selecting a first element and a second element comprises using programmed logic.

12. The method recited in claim 11 wherein the programmed logic is contained within one of a general purpose computer, microprocessor, and FPGA coupled to the detector elements.

13. The method recited in claim 1 wherein the light beam is focused on the photomask or wafer.

14. The method recited in claim 13 further comprising obtaining the sum of the first and second signal to produce a resulting second signal indicating whether there is a defect present.

15. The method recited in claim 14 further comprising repeating the operations of claim 14 for a plurality of locations on the photomask or wafer to generate simultaneously a differential image signal and a summed image signal.

16. The method recited in claim 1 wherein the detector further comprises a first band of detector elements surrounding the central region.

17. The method recited in claim 16 wherein the first band of detector elements is arranged in a first annular region.

18. The method recited in claim 16 wherein the detector further comprises a second band of detector elements surrounding the first band.

19. The method recited in claim 18 wherein the second band of detector elements is arranged in a second annular region.

20. The method recited in claim 19 wherein each detector element in the central region, the first band and the second band of detector elements is arranged about the center of the detector in a radially symmetric configuration and is defined by an angular sector having a center at the detector center.

21. A scanning optical microscopy system configured to detect phase defects in a semiconductor processing photomask or wafer comprising:

an optical beam generator to direct a light beam towards a surface of the semiconductor processing mask or wafer;

a detector comprising at least four elements, wherein at least a first element and a second element of the at least four elements are used to generate respectively a first signal and a second signal, wherein the first element and the second element are selected to correspond to the orientation of opaque pattern lines on the photomask or wafer in the proximity of the first light beam location on the photomask or wafer; and an analyzer configured to obtain the difference between the first signal and the second signal to produce a resulting signal indicating whether there is a defect present.

22. The scanning optical microscopy system recited in claim 21 wherein the light beam is focused on the photomask or wafer.

23. The scanning optical microscopy system recited in claim 21 wherein the detector is configured to provide a signal corresponding to the light collected at any selected one of the quadrants of the detector isolated from the light collected from the other 3 quadrants.

24. The scanning optical microscopy system recited in claim 21 wherein the at least four elements are configured in a Cartesian grid pattern.

25. The scanning optical microscopy system recited in claim 21 wherein the at least four elements are configured in a polar grid pattern.

26. The scanning optical microscopy system recited in claim 21 wherein the at least a first element comprises a first element and a third element and the at least a second element comprises a second element and a fourth element.

27. The scanning optical microscopy system recited in claim 21 wherein the detector comprises a central region having at least 4 elements.

28. The scanning optical microscopy system recited in claim 21 wherein the central region comprises a circular region about the center of the detector.

29. The scanning optical microscopy system recited in claim 21 wherein the analyzer is one of a general purpose computer, microprocessor, and FPGA.

30. The scanning optical microscopy system recited in claim 21 wherein the analyzer is further configured to repeat the operations of claim 21 for a plurality of locations on the photomask or wafer to generate an image signal and comparing the image signal to a similar pattern location on one of a same die on the photmask or wafer, another die on the photomask or wafer, or a pattern from a design database to identify defects.

31. The scanning optical microscopy system recited in claim 21 wherein the analyzer is further configured to select a first element and a second element comprises using programmed logic.

32. The scanning optical microscopy system recited in claim 31 wherein the analyzer is further configured to move the light beam to a second location on the photomask or wafer and repeat selecting a first element and a second element in accordance with the state of the programmed logic.

33. The scanning optical microscopy system recited in claim 21 wherein the analyzer is further configured to obtain the sum of the first and second signal to produce a resulting second signal indicating whether there is a defect present.

34. The scanning optical microscopy system recited in claim 33 further configured to obtain the resulting signal and the resulting second signal for each inspected location on the photomask or wafer.

35. The scanning optical microscopy system recited in claim 21 wherein the detector further comprises a first band of detector elements surrounding the central region.

36. The scanning optical microscopy system recited in claim 35 wherein the first band of detector elements is arranged in a first annular region.

37. The scanning optical microscopy system recited in claim 35 wherein the detector further comprises a second band of detector elements surrounding the first band.

38. The scanning optical microscopy system recited in claim 37 wherein the second band of detector elements is arranged in a second annular region.

39. The scanning optical microscopy system recited in claim 38 wherein each detector element in the central region, the first band and the second band of detector elements is arranged about the center of the detector in a radially symmetric configuration and is defined by an angular sector having a center at the detector center.

40. A method for detecting phase defects in an inspected object during semiconductor processing, using an illumination imaging system, the method comprising:

generating illumination from at least one source configured to illuminate the inspection object from at least 4 different directions;

collecting the illumination corresponding to at least a first and second of the at least 4 different directions, wherein the illumination is reflected from or transmitted through the inspection object at a detector; and providing a differential signal from the collected illumination corresponding to the first direction and the collected illumination corresponding to the second direction.

41. The method recited in claim 40 wherein the illumination is focused on the inspected object.

42. The method recited in claim 40 wherein the illumination is provided by 4 different apertures in 4 different locations.

43. The method recited in claim 40 wherein the illumination is collected sequentially from each aperture.

* * * * *